(12) United States Patent
Kuhn et al.

(10) Patent No.: US 8,752,722 B2
(45) Date of Patent: Jun. 17, 2014

(54) CAP ASSEMBLY AND PRODUCTION METHOD

(75) Inventors: Peter Kuhn, Heiligenschwendi (CH); Gallus Egli, Bleiken (CH); Philippe Kern, Rubigen (CH); Mario Schüpbach, Zäziwil (CH); Ludwig Daniel Weibel, Waldstatt (CH)

(73) Assignee: Vifor (International) AG, St. Gallen (CH)

( * ) Notice: Subject to any disclaimer, the term of this patent is extended or adjusted under 35 U.S.C. 154(b) by 272 days.

(21) Appl. No.: 13/120,491

(22) PCT Filed: Sep. 29, 2008

(86) PCT No.: PCT/EP2008/063036
§ 371 (c)(1),
(2), (4) Date: Oct. 31, 2011

(87) PCT Pub. No.: WO2010/034356
PCT Pub. Date: Apr. 1, 2010

(65) Prior Publication Data
US 2012/0031904 A1    Feb. 9, 2012

(51) Int. Cl.
*B65D 41/02*    (2006.01)
*B65D 17/34*    (2006.01)
*B65D 55/02*    (2006.01)

(52) U.S. Cl.
USPC ........... 220/265; 220/260; 220/266; 220/269; 215/216; 215/250; 206/364

(58) Field of Classification Search
USPC .............. 220/260, 265, 269; 215/216, 250, 215/DIG. 3; 206/363, 364; 604/111
See application file for complete search history.

(56) References Cited

U.S. PATENT DOCUMENTS 5,540,666 A * 7/1996 Barta et al. .............. 604/192
6,129,711 A   10/2000 Speck
(Continued)

FOREIGN PATENT DOCUMENTS

EP    1433705    6/2004
FR    2786106    5/2000

OTHER PUBLICATIONS

Espacenet bibliographic data for FR 2786106 published May 26, 2000, two pages.

(Continued)

*Primary Examiner* — Fenn Mathew
*Assistant Examiner* — Madison L Poos
(74) *Attorney, Agent, or Firm* — Rankin, Hill & Clark LLP

(57) ABSTRACT

The invention relates to a tip cap assembly for closing a distal opening of a receptacle like a syringe body or a tube in a sealed manner, and to a method for producing the tip cap. A cap assembly according to the invention comprises a frangible tip of a receptacle, preferably a pre-filled receptacle. An upper portion of the tip closes the receptacle respectively a lower tip portion comprising a passage as known from the state of the art. Hence, the receptacle is reliably sealed to prevent contamination or loss of the medication. Compared with the state of the art, a receptacle has a more effectively sealed tip. It is necessary to break the upper tip portion away in order to open the receptacle. A cap element protects the tip on one side. On the other side, unscrewing the cap breaks the upper portion away without hurting a person.

12 Claims, 4 Drawing Sheets

(56) References Cited

U.S. PATENT DOCUMENTS

| | | | |
|---|---|---|---|
| 2001/0003150 A1* | 6/2001 | Imbert | 604/256 |
| 2005/0283116 A1 | 12/2005 | Eakins et al. | |
| 2006/0178627 A1 | 8/2006 | Geiger et al. | |
| 2009/0149817 A1 | 6/2009 | Frezza | |

OTHER PUBLICATIONS

International Preliminary Report on Patentability for corresponding PCT/EP2008/063036 mailed Sep. 13, 2010, 10 pages.

* cited by examiner

CAP ASSEMBLY AND PRODUCTION METHOD

The invention relates to a tip cap assembly for closing a distal opening of a receptacle like a syringe body or a tube in a sealed manner, and to a method for producing the tip cap.

Conventional syringes each include a barrel having an open proximal end and an opposed distal. A cylindrical wall extends between the ends and defines a substance retaining chamber. An elongate tip projects from the distal end of the syringe barrel and includes a narrow passage which communicates with the substance retaining chamber of the barrel. A plunger may be inserted into the open proximal end of the syringe barrel for sliding fluid-tight engagement with the cylindrical chamber wall. Sliding movement of the plunger in a distal direction urges fluid in the chamber through the passage in the tip. Conversely, sliding movement of the plunger in a proximal direction draws fluid through the passage in the tip and into the chamber of the syringe barrel.

Conventional syringe barrels typically are made of plastic or glass. Glass exhibits lower gas transmissivity than plastic. Thus, glass syringe barrels are used for medications that are particularly susceptible to interaction with ambient gases. Glass syringe barrels also are preferably used for medications that are pre-filled into the syringe barrel and stored for a considerable period of time prior to use.

Such syringes may further include a needle assembly with a needle cannula having a proximal end, a pointed distal end and a lumen extending axially therethrough. The needle assembly also includes a hub which is engage able with mounting means on the syringe barrel for selectively placing the lumen of the needle cannula in fluid communication with the passage through the tip of the syringe barrel.

One prior mounting means includes a luer collar disposed in spaced concentric relationship around the tip of the syringe barrel. The luer collar includes an array of threads for threaded engagement with corresponding structure on the hub of the needle. For example, the luer collar may include an array of internal threads which are engageable with projections extending outwardly from the hub of the needle cannula. Syringe barrels formed from plastic may have the luer collar unitarily molded therewith. However, glass syringe barrels may not be easily formed with a unitary luer collar. Thus, glass syringe barrels and some plastic syringe barrels may have a separately formed luer collar securely mounted to the tip of the syringe barrel. The luer collar may rely upon a slip fit engagement, a snap fit or other such secure mounting engagement around the tip of the syringe barrel.

Medications that are pre-filled into a syringe barrel must be sealed to prevent contamination or loss of the medication. Seals also prevent health care workers from being needlessly exposed to medications. The prior devices have included stoppers or closures mounted over the tip at the distal end of the syringe barrel to prevent leakage and to avoid contamination of the medication. Prior tip caps have been formed from elastomeric material frictionally and/or resiliently retained in engagement with the tip of the prior syringe barrel. The prior tip cap may be removed from the syringe tip shortly prior to usage of the syringe. The hub of the needle assembly may then be securely engaged with the luer collar or other mounting means adjacent the exposed tip of the syringe barrel. For example, the needle hub may be threadedly engaged within the luer collar such that the lumen of the prior needle cannula communicates with the exposed tip of the prior syringe barrel.

Prior elastomeric tip caps on the ends of pre-filled syringe barrels generally perform well. However, the resiliently and/or frictionally engaged type tip cap may be accidentally disengaged from the tip of the syringe barrel in response to inadvertent forces imposed thereon or due to dimensional changes or instability of the elastomeric seal. Additionally, the vacuum or suction effect created as the prior elastomeric tip cap is removed from the tip of the syringe barrel can lead to the loss of medication and unnecessary personal contact with medication that the tip cap is intended to avoid. Additionally, the prior elastomeric tip cap provides no evidence of tampering or misuse of a pre-filled syringe.

U.S. Pat. No. 6,190,364 describes a syringe tip cap for a syringe body. The syringe body has a distal tip and a distal opening extending through the latter, such that an injection liquid located in the syringe body can exit the syringe body via the distal opening. The syringe comprises a fastening ring, or luer collar, which is formed in one piece with the syringe or is placed on the distal tip of the syringe body and connected fixedly thereto. The fastening ring has thread elements which interact with thread elements of a two-part closure cap in order to hold the closure cap on the fastening ring. In use, the closure cap encloses the distal tip and closes and seals off the distal opening of the syringe body.

To inject the injection liquid, the closure cap is unscrewed from the fastening ring and a syringe needle is secured on the fastening ring and thus on the syringe body in such a way that a needle opening extending through the syringe needle is in fluidic communication with the distal opening of the syringe body. To secure the syringe needle on the fastening ring, the syringe needle is connected to a thread element which interacts with the thread element of the fastening ring.

To ensure that possible use of or tampering with the syringe content is made evident, the syringe tip cap according to U.S. Pat. No. 6,190,364 comprises a sealing strip which is connected permanently both to the fastening ring and also to the closure cap, such that the sealing strip tears when the closure cap is detached from the fastening ring.

A disadvantage of the syringe tip cap known from U.S. Pat. No. 6,190,364 is that producing three separate parts (two-part closure cap, sealing element) and joining these parts together to form a syringe tip cap is an elaborate procedure.

US 2006/0178627 A1 discloses a syringe tip cap for sealingly closing a distal opening of a syringe body. The syringe tip cap comprises a fastening ring to be arranged and fastened on the syringe body about the distal opening. A closure cap is releasably connected to the fastening ring and closes the distal opening. The fastening ring has a first locking device interlocked with a second locking device of the closure cap. The first locking device and the second locking device are configured not to be unlocked without sustaining damage. After unlocking, the syringe tip cap cannot be returned to an initial locked state.

The German company Gerresheimer AG from Düsseldorf, is selling syringe tip caps according to the caps known from US 2006/0178627 A1. The practice has shown that it is possible to disengage the fastening ring of the caps from the syringe body after opening of the syringe. After disengaging the fastening ring, it is possible to lock the first locking device with the second locking without sustaining damage. Afterwards, it is possible to engage the fastening ring with the syringe body. As a result, it is not possible to ensure that possible use of or tampering with the syringe content is made evident.

Thus, there is a need for a cap assembly which would eliminate at least one of the problems and limitations associated with the prior art cap assemblies discussed above.

Figure 1:
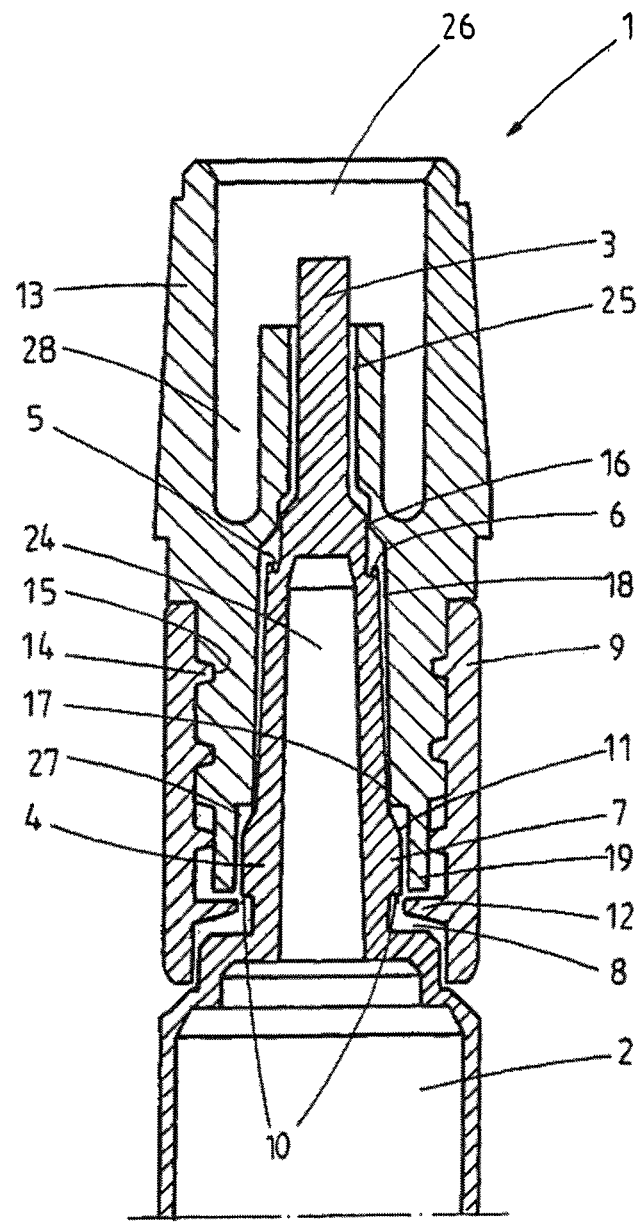
FIG. 1 depicts a cross-sectional view of a cap assembly of the invention.
Figure 2:
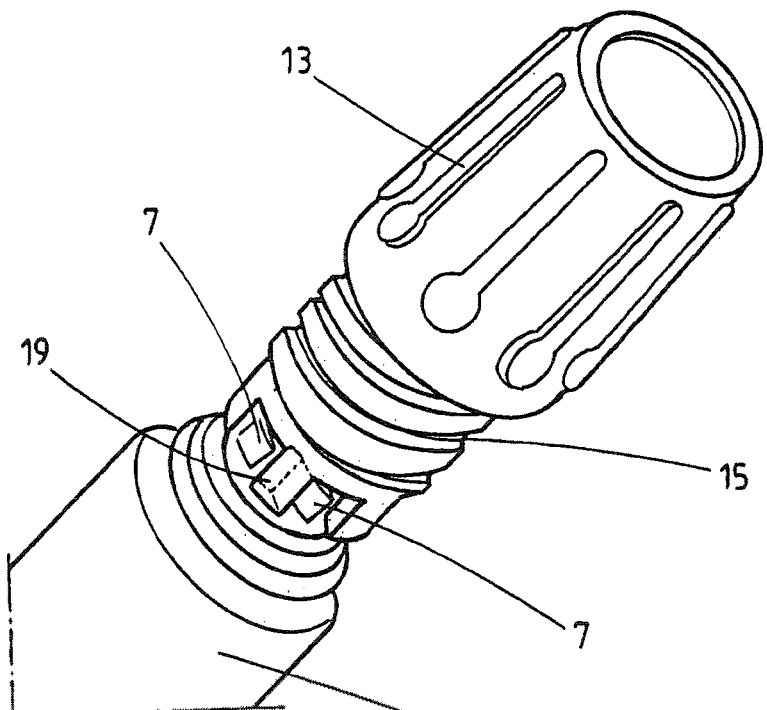
FIG. 2 depicts a perspective view of a cap assembly of the invention.

In order to solve one of the above mentioned problems, a cap assembly according to the invention comprises a tip of a receptacle, preferably a pre-filled receptacle.

Preferably, the tip is frangible and comprises a predetermined breaking point. An upper portion of the tip closes the receptacle respectively a lower tip portion comprising a passage as known from the state of the art. Hence, the receptacle is reliably sealed to prevent contamination or loss of the medication. Compared with the state of the art, a receptacle has a more effectively sealed tip. It is necessary to break the upper tip portion away in order to open the receptacle. A cap element protects the tip on one side. On the other side, unscrewing the cap breaks the upper portion away without hurting a person.

Typically, the receptacle is a syringe or a tube. As a rule, the syringe or tube volume is up to 100 ml, preferably up to 30 ml.

In a preferred embodiment of the invention, the predetermined breaking point is concave and borders on the upper angular edge of the passage of the lower tip portion. As a result, breaking the upper tip portion away cannot damage the angular edge of the passage.

In an embodiment of the invention, the tip of a cap assembly comprises a plurality of projecting locking elements for attaching a fastening ring like a luer collar. Due to the luer collar, it is possible to screw a further cap element on the receptacle which may protect at least an upper portion of the tip. The cap assembly according to this embodiment may comprise an upper tip portion or a separate cap element closing the opening of the receptacle.

The projecting locking elements may provide a plurality of clearances in order to hold the fastening ring in appropriate manner. Preferably, the clearances are so designed that it is not possible to unfasten a fastening ring attached at the receptacle or at the tip portion without sustaining damage. This embodiment of the invention is suited for evidencing tampering or misuse of a pre-filled receptacle. On the other hand, the projecting locking elements are so designed that it is possible to fasten the fastening ring to the receptacle by a snapping action as already known from the state of the art.

Preferably, the cap element is attached at the fastening ring by an internal and an external thread or a bayonet joint. The cap element 13 comprises a plurality of locking tabs. In the closed position of the cap assembly, the locking tabs are enclosed with a form fit by locking recesses provided by projecting locking elements. The locking tabs and the corresponding locking recesses or the projecting locking elements are so designed that it is not possible to screw the cap element (13) on the tip. In contrast to the state of the art, the cap assembly evidences tampering or misuse of the syringe in all cases.

The various features, objects, benefits and advantages of the present invention will become more apparent upon reading the following detailed description of the preferred embodiment along with the appended claims in conjunction with the drawings.

FIG. 1 shows an embodiment of the invention, a cap assembly 1 comprising a frangible tip of a receptacle 2. The receptacle may be a syringe or a tube. The tip is composed of an upper tip portion 3, a lower tip portion 4 and a predetermined breaking point 5 between the upper and the lower tip portion. The tip is frangible due to the predetermined breaking point 5. The lower tip portion looks like a hollow needle comprising a canal 24. The tip is made in one piece and closes the receptacle respectively the distal end of the canal 24. Breaking the upper tip portion 3 opens the receptacle 2 respectively the distal end of the canal 24. Hence, the upper tip portion acts as a closure of the receptacle. Since the tip is made in one piece, it is impossible that the closure of the receptacle comprises a leak or something like that. The predetermined breaking point 5 is concave and borders on the upper angular edge 6 of the lower tip portion 4. Breaking the upper tip portion will not damage the upper angular edge 6. Hence, after opening the receptacle there is an undamaged distal tip opening as known from a syringe and the like.

The lower tip portion comprises a plurality of projecting locking elements 7 adjacent at the body 2 of the receptacle. The projecting locking elements 7 and the lower tip portion 4 are made in one piece. The projecting locking elements 7 provide a plurality of clearances 8 for attaching a fastening ring 9 to the receptacle respectively to the lower tip portion 4. These clearances are between the projecting locking elements 7 and the main body of the receptacle. The projecting locking elements 7 are so designed that it is possible to fasten the fastening ring 9 to the receptacle by a snapping action. However, it is not possible to unfasten the fastening ring without sustaining damage. For this reason, the angles between the lower side walls 10 of the projecting locking elements 7 and the adjacent side wall of the lower tip portion 4 are 90° or smaller. The opposite side walls 11 of the projecting locking elements 7 are inclined and act as ramp with regard to an annular protrusion 12 of the fastening ring 9.

The annular protrusion 12 attaching the fastening ring to the receptacle is inside of the fastening ring 9. The annular protrusion 12 and the fastening ring are made in one piece.

The cap assembly 1 comprises a cap element 13. The fastening ring 9 and the cap element 13 comprise interacting thread elements 14 and 15 which define a thread pitch. Due to the thread elements 14 and 15, it is possible to open the receptacle by unscrewing the cap element 13. A ring-like portion acting as a seal 16 of the cap element 13 is pressed against the upper tip portion 3, acts as a seal and grips the upper tip portion 3. For this reason, unscrewing of the cap element 13 breaks the predetermined breaking point 5 and opens the receptacle. There is a further ring-like portion acting as a seal 17 which is pressed against the lower tip portion 4 acting as a seal. There remains a well-defined cavity 18 between the two ring-like portions acting as seals 16 and 17. Hence, contamination of the lower tip portion including the edge 6 within the well-defined cavity is not possible.

Due to the conical profile of the lower tip portion 4 unscrewing of the cap element 13 removes the lower ring-like portion acting as a seal 17 from the lower tip portion at once. For this reason, the lower ring-like portion acting as a seal 17 cannot prevent unscrewing of the cap element 13.

Figure 3:
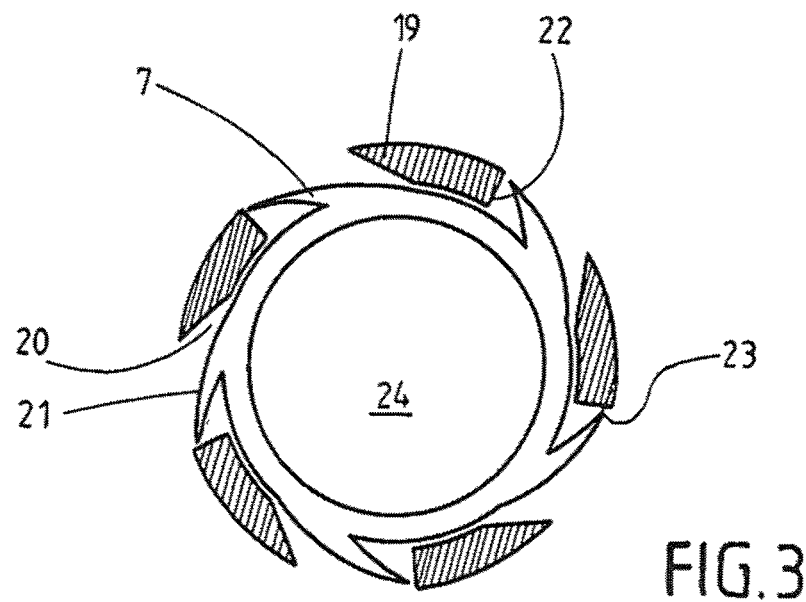
FIG. 3 depicts a cross-sectional view of a cap assembly of the invention.

The cap element 13 comprises a plurality of locking tabs 19. In the closed position of cap assembly 1, the locking tabs 19 are enclosed with a form fit by locking recesses 20. The locking recesses are provided by the projecting locking elements 7. In contrast to the teaching known from US 2006/0178627 A1, the locking tabs 19 and the corresponding locking recesses will not irreversibly deformed or damaged by unscrewing the cap element 13. As shown in FIG. 3, the locking tabs 19 and the corresponding locking recesses 20 respectively the projecting locking elements 7 are so designed that it is not possible to screw the cap element 13 on the tip 3 and 4. Due to the inclinations 21, it is possible to unscrew the cap element 13. However, due to the stopping portions 22 and the tips 23 of the projecting locking elements 7, it is impossible to screw the cap element 13 on the tip of the receptacle 2.

A cylinder-like gap 25 remains between the cap element 13 and the upper tip portion 3. The cylinder-like gap 25 extends to the seal 16 on one side and to an opening 26 on the other side. It is possible to evacuate the opening in order to check the operability of the seal 16. In a similar way, it is possible to evacuate an opening 27 leading to the ring-like portion acting as a seal 17 in order to check the operability of the ring-like portion acting as a seal 17.

Figure 4:
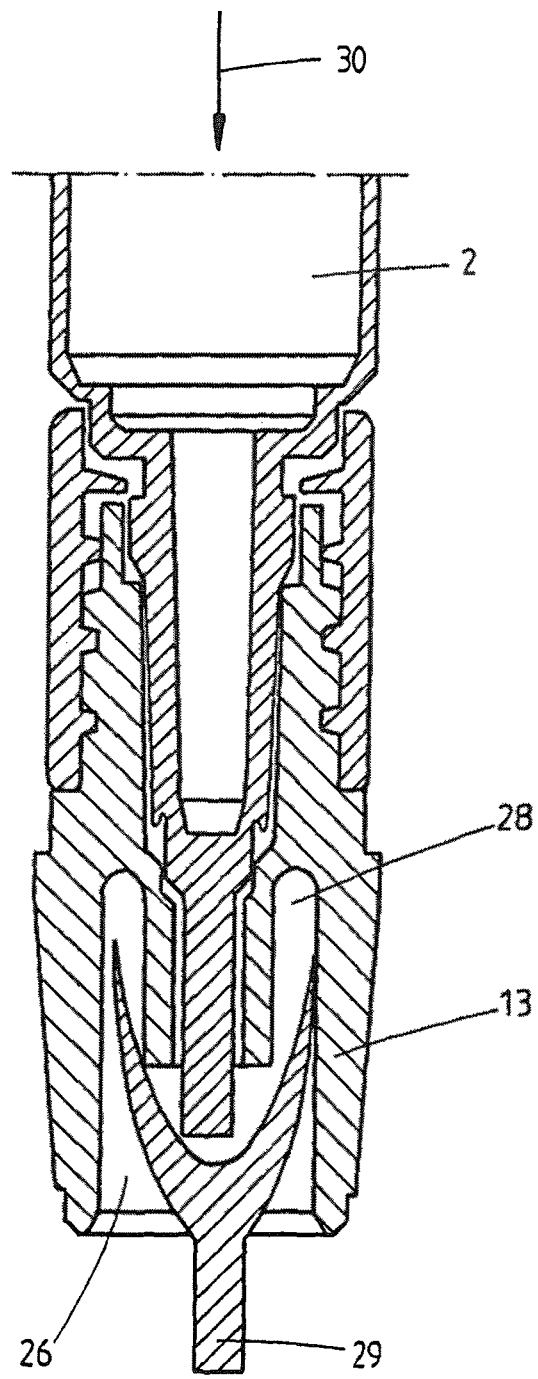
FIG. 4 depicts a cross-sectional view of a cap assembly of the invention.

The cap element 13 comprises a cylinder-like recess 28 surrounding the upper tip portion 3. Due to the cylinder-like recess 28, it is possible to grip the cap assembly 1 from the bottom for example by a pinion 29 as shown in FIG. 4. It is then possible to fill the receptacle with a medical preparation from the top according to the arrow 30 without running into problems. In order to avoid a contamination, there is as a rule a laminar gas flow in the direction of the arrow 30 during filling the receptacle. For this reason, means for handling the receptacle in the upper region during filling the receptacle are able to disturb the process. Due to the cylinder-like recess 28, handling means in the upper region are not necessary. After filling the receptacle 2, the corresponding end will be closed for example by welding or a corresponding method.

Preferably, the receptacle 2 as well as the cap assembly 1 are made of plastic.

Figure 5:
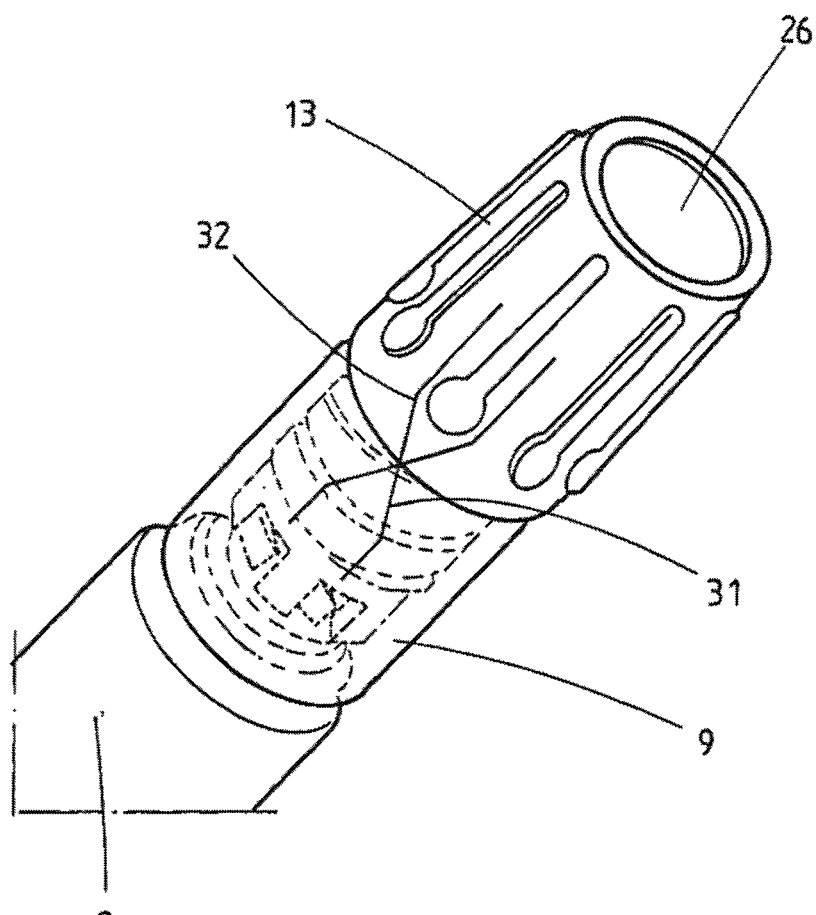
FIG. 5 depicts a perspective view of a cap assembly of the invention.

FIG. 5 shows the cap assembly 1 comprising a transparent fastening ring 9. As a result, it is possible to see the position of the locking tabs 19. The fastening ring 9 comprises a visible sign respectively a visible mark. The cap element 13 comprises a corresponding visible sign 32. If the tips of the two signs 31 and 32 are in line as shown in FIG. 5 and if there is no visible gap between the cap element 3 and the fastening ring 9, nobody tried to open the receptacle.

Providing the cap assembly 1 is very easy. At the beginning, the cap element 13 will be screwed on the fastening ring 9. Afterwards, the fastening ring 9 will be pushed against the corresponding end of the body of the receptacle 2 thereby providing a snap-in connection between the projecting locking elements 7 and the annular protrusion 12. Afterwards, it is not possible remove the fastening ring 9 from the receptacle. For this reason, it is not possible to close the receptacle by the cap assembly 1 once again.

The invention claimed is:

1. A cap assembly comprising a frangible tip of a receptacle, a fastening ring and a cap element attached to the fastening ring by an internal and one of an external thread and a bayonet joint, wherein, the fastening ring is attached at the receptacle or a lower tip portion of the tip by an annular protrusion and wherein, the cap element comprises a plurality of locking tabs, wherein in a closed position of the cap assembly the locking tabs are enclosed with a form fit by locking recesses provided by projecting locking elements wherein the frangible tip is an integral part of the receptacle and wherein the lower tip portion of the tip of the cap assembly comprises a plurality of projecting locking elements adjacent to a body of the receptacle for attaching the fastening ring either to the receptacle or to the lower tip portion.

2. The cap assembly according to claim 1, wherein the projecting locking elements and the lower tip portion are made in one piece.

3. The cap assembly according to claim 1, wherein the projecting locking elements provide a plurality of clearances for attaching the fastening ring to the receptacle or to the lower tip portion.

4. The cap assembly according to claim 1, wherein the cap assembly is composed of an artificial material.

5. The cap assembly according to claim 1, wherein the cap assembly further comprises a transparent fastening ring.

6. The cap assembly according to claim 1, wherein the fastening ring and the cap element comprise visible signs which are in line.

7. A receptacle comprising the cap assembly of claim 1, wherein the receptacle is prefilled with a medical preparation.

8. A cap assembly comprising a frangible tip of a receptacle, a fastening ring and a cap element attached to the fastening ring by an internal and one of an external thread and a bayonet joint, wherein, the fastening ring is attached at the receptacle or a lower tip portion of the tip by an annular protrusion and wherein, the cap element comprises a plurality of locking tabs, wherein in a closed position of the cap assembly the locking tabs are enclosed with a form fit by locking recesses provided by projecting locking elements, wherein the frangible tip is an integral part of the receptacle and wherein the lower tip portion of the tip further comprises a plurality of projecting locking elements which are so designed that it is possible to fasten the fastening ring to the receptacle by a snapping action.

9. A cap assembly comprising a frangible tip of a receptacle, a fastening ring and a cap element attached to the fastening ring by an internal and one of an external thread and a bayonet joint, wherein, the fastening ring is attached at the receptacle or a lower tip portion of the tip by an annular protrusion and wherein, the cap element comprises a plurality of locking tabs, wherein in a closed position of the cap assembly the locking tabs are enclosed with a form fit by locking recesses provided by projecting locking elements, wherein the frangible tip is an integral part of the receptacle and wherein a cylinder-like gap remains between the cap element and an upper tip portion extending to a seal on one side and to an opening on the other side.

10. A cap assembly comprising a frangible tip of a receptacle, a fastening ring and a cap element attached to the fastening ring by an internal and one of an external thread and a bayonet joint, wherein, the fastening ring is attached at the receptacle or a lower tip portion of the tip by an annular protrusion and wherein, the cap element comprises a plurality of locking tabs, wherein in a closed position of the cap assembly the locking tabs are enclosed with a form fit by locking recesses provided by projecting locking elements, wherein the frangible tip is an integral part of the receptacle and wherein a cap element comprises a cylinder-like recess surrounding an upper tip portion of the tip.

11. A cap assembly comprising a frangible tip of a receptacle, a fastening ring and a cap element attached to the fastening ring by an internal and one of an external thread and a bayonet joint, wherein, the fastening ring is attached at the receptacle or a lower tip portion of the tip by an annular protrusion and wherein, the cap element comprises a plurality of locking tabs, wherein in a closed position of the cap assembly the locking tabs are enclosed with a form fit by locking recesses provided by projecting locking elements, wherein the frangible tip is an integral part of the receptacle and wherein the cap assembly comprises a sealed cavity which prevents contamination of a lower tip portion and an upper edge of the lower tip portion.

12. A method for providing a cap assembly, the cap assembly comprising a frangible tip of a receptacle, a fastening ring and a cap element attached to the fastening ring by an internal and one of an external thread and a bayonet joint, wherein, the fastening ring is attached at the receptacle or a lower tip portion of the tip by an annular protrusion and wherein, the cap element comprises a plurality of locking tabs, wherein in a closed position of the cap assembly the locking tabs are enclosed with a form fit by locking recesses provided by projecting locking elements, wherein the frangible tip is an integral part of the receptacle, the method comprising:
- (a) screwing a cap element which comprises a plurality of locking tabs, onto a fastening ring, and
- (b) pushing the fastening ring against an end of a body of a receptacle comprising a frangible tip thereby providing a snap-in connection between projecting locking elements of the frangible tip and an annular protrusion of the fastening ring and a form fit connection between the projecting locking elements and the locking tabs.

* * * * *